(12) United States Patent
Pigott et al.

(10) Patent No.: US 12,408,932 B2
(45) Date of Patent: Sep. 9, 2025

(54) INTRAVASCULAR DEVICE HAVING FEEDBACK ELEMENTS

(71) Applicant: VentureMed Group, Inc., Plymouth, MN (US)

(72) Inventors: John P. Pigott, Sylvania, OH (US); Jenny Zeroni, Plymouth, MN (US); Adam Tschida, Brooklyn Park, MN (US)

(73) Assignee: VentureMed Group, Inc., Plymouth, MN (US)

( * ) Notice: Subject to any disclaimer, the term of this patent is extended or adjusted under 35 U.S.C. 154(b) by 314 days.

(21) Appl. No.: 17/702,336

(22) Filed: Mar. 23, 2022

(65) Prior Publication Data

US 2023/0301670 A1 Sep. 28, 2023

(51) Int. Cl.
*A61B 17/22* (2006.01)
*A61B 17/00* (2006.01)

(52) U.S. Cl.
CPC ........ *A61B 17/22* (2013.01); *A61B 17/00234* (2013.01); *A61B 2017/00199* (2013.01); *A61B 2017/00336* (2013.01); *A61B 2017/22001* (2013.01); *A61B 2017/22048* (2013.01); *A61B 2017/22051* (2013.01);
(Continued)

(58) Field of Classification Search
CPC .............. A61B 17/00234; A61B 17/22; A61B 17/320725; A61B 2017/00022; A61B 2017/00115; A61B 2017/00199; A61B 2017/00336; A61B 2562/0247; A61B 2562/0261; A61B 2562/04; A61B 2017/22001; A61B 2017/22048; A61B 2017/22051; A61B 2017/22061; A61B 2090/064; A61B 2090/0811; A61M 2025/0166

See application file for complete search history.

(56) References Cited

U.S. PATENT DOCUMENTS 2,655,154 A 10/1953 Richter
3,557,794 A 1/1971 Van Patten
(Continued)

FOREIGN PATENT DOCUMENTS

EP 0727194 A1 8/1996
WO 8102109 A1 8/1981
(Continued)

OTHER PUBLICATIONS

Cardiovascular Systems Inc., Diamondback 360 Coronary Orbital Atherectomy System, http://www.csi360.com/products/coronary-diamondback-360-coronary-orbital-atherectomy-system-crowns/, 2016.
(Continued)

*Primary Examiner* — Mohamed G Gabr
(74) *Attorney, Agent, or Firm* — Standley Law Group LLP; Adam J. Smith; Jeffrey S. Standley

(57) ABSTRACT

An intravascular device for providing feedback to an operator during use and methods of providing the same as disclosed. A catheter tube extends from a handle assembly. An expandable portion is connected to the catheter tube and is selectively movable between a first position and an expanded position. A feedback device provided at the expandable portion provides the operator with the feedback.

20 Claims, 6 Drawing Sheets

(52) U.S. Cl.
CPC ........... *A61B 2562/0247* (2013.01); *A61B 2562/0261* (2013.01); *A61B 2562/04* (2013.01)

(56) References Cited

U.S. PATENT DOCUMENTS

| | | | |
|---|---|---|---|
| 3,704,711 A | 12/1972 | Park | |
| 4,273,128 A | 6/1981 | Banning | |
| 4,292,974 A | 10/1981 | Fogarty et al. | |
| 4,654,027 A | 3/1987 | Dragan et al. | |
| 5,030,201 A | 7/1991 | Palestrant | |
| 5,074,817 A | 12/1991 | Song | |
| 5,074,871 A | 12/1991 | Groshong | |
| 5,100,425 A | 3/1992 | Fischell et al. | |
| 5,154,724 A | 10/1992 | Andrews | |
| 5,156,610 A | 10/1992 | Reger | |
| 5,178,625 A | 1/1993 | Groshong | |
| 5,211,651 A | 5/1993 | Reger et al. | |
| 5,224,945 A | 7/1993 | Pannek, Jr. | |
| 5,244,619 A | 9/1993 | Burnham | |
| 5,246,421 A | 9/1993 | Saab | |
| 5,250,060 A | 10/1993 | Carbo et al. | |
| 5,282,484 A | 2/1994 | Reger | |
| 5,312,427 A | 5/1994 | Shturman | |
| 5,318,576 A | 6/1994 | Plassche, Jr. et al. | |
| 5,376,100 A | 12/1994 | Lefebvre | |
| 5,514,093 A | 5/1996 | Ellis et al. | |
| 5,591,194 A | 1/1997 | Berthiaume | |
| 5,658,309 A | 8/1997 | Berthiaume et al. | |
| 5,665,098 A | 9/1997 | Kelly et al. | |
| 5,676,654 A | 10/1997 | Ellis et al. | |
| 5,697,944 A | 12/1997 | Lary | |
| 5,697,948 A | 12/1997 | Marin et al. | |
| 5,728,067 A | 3/1998 | Enger | |
| 5,728,123 A | 3/1998 | Lemelson et al. | |
| 5,733,296 A | 3/1998 | Rogers et al. | |
| 5,766,192 A | 6/1998 | Zacca | |
| 5,792,158 A | 8/1998 | Lary | |
| 5,800,450 A | 9/1998 | Lary et al. | |
| 5,836,868 A | 11/1998 | Ressemann et al. | |
| 5,876,448 A | 3/1999 | Thompson et al. | |
| 5,961,536 A | 10/1999 | Mickley et al. | |
| 5,968,064 A | 10/1999 | Selmon et al. | |
| 6,071,287 A | 6/2000 | Verbeek | |
| 6,120,515 A | 9/2000 | Rogers et al. | |
| 6,129,708 A | 10/2000 | Enger | |
| 6,165,187 A | 12/2000 | Reger | |
| 6,217,549 B1 | 4/2001 | Selmon et al. | |
| 6,258,108 B1 | 7/2001 | Lary | |
| 6,270,489 B1 | 8/2001 | Wise et al. | |
| 6,283,947 B1 | 9/2001 | Mirzaee | |
| 6,527,740 B1 | 3/2003 | Jackson et al. | |
| 6,599,267 B1 | 7/2003 | Ray et al. | |
| 6,692,466 B1 | 2/2004 | Chow et al. | |
| 6,695,863 B1 | 2/2004 | Ramzipoor et al. | |
| 6,719,773 B1 | 4/2004 | Boucher et al. | |
| 6,884,257 B1 | 4/2005 | Cox | |
| 7,108,704 B2 | 9/2006 | Trerotola | |
| 7,131,981 B2 | 11/2006 | Appling et al. | |
| 7,172,614 B2 | 2/2007 | Boyle et al. | |
| 7,279,002 B2 | 10/2007 | Shaw et al. | |
| 7,303,572 B2 | 12/2007 | Melsheimer et al. | |
| 7,329,267 B2 | 2/2008 | Weber | |
| 7,517,352 B2 | 4/2009 | Evans et al. | |
| 7,686,824 B2 | 3/2010 | Konstantino et al. | |
| 7,691,086 B2 | 4/2010 | Tkebuchava | |
| 7,708,753 B2 | 5/2010 | Hardert | |
| 7,850,685 B2 | 12/2010 | Kunis et al. | |
| 7,850,710 B2 | 12/2010 | Huss | |
| 7,887,557 B2 | 2/2011 | Kelley et al. | |
| 7,914,549 B2 | 3/2011 | Morsi | |
| 7,955,350 B2 | 6/2011 | Konstantino et al. | |
| 8,308,754 B2 | 11/2012 | Belson | |
| 8,323,307 B2 | 12/2012 | Hardert | |
| 8,328,829 B2 | 12/2012 | Olson | |
| 8,348,987 B2 | 1/2013 | Eaton | |
| 8,366,661 B2 | 2/2013 | Weber et al. | |
| 8,398,662 B2 | 3/2013 | Granada et al. | |
| 8,430,904 B2 | 4/2013 | Belson | |
| 8,454,636 B2 | 6/2013 | Konstantino et al. | |
| 8,500,789 B2 | 8/2013 | Wuebbeling et al. | |
| 8,685,049 B2 | 4/2014 | Schur et al. | |
| 8,685,050 B2 | 4/2014 | Schur et al. | |
| 8,702,736 B2 | 4/2014 | Schur et al. | |
| 8,740,849 B1 | 6/2014 | Fischell et al. | |
| 8,870,816 B2 | 10/2014 | Chambers et al. | |
| 8,968,354 B2 | 3/2015 | Wang et al. | |
| 8,974,490 B2 | 3/2015 | Jonsson | |
| 9,039,727 B2 | 5/2015 | Kusleika | |
| 9,079,000 B2 | 7/2015 | Hanson et al. | |
| 9,192,747 B2 | 11/2015 | Hardert | |
| 9,282,991 B2 | 3/2016 | Schur et al. | |
| 9,314,329 B2 | 4/2016 | Dickinson et al. | |
| 9,364,255 B2 | 6/2016 | Weber | |
| 9,364,284 B2 | 6/2016 | Groff et al. | |
| 9,510,901 B2 | 12/2016 | Steinke et al. | |
| 9,532,798 B2 | 1/2017 | Schur et al. | |
| 9,545,263 B2 | 1/2017 | Lenihan et al. | |
| 9,592,386 B2 | 3/2017 | Mathur et al. | |
| 9,604,036 B2 | 3/2017 | Burton et al. | |
| 9,615,848 B2 | 4/2017 | Pigott | |
| 10,463,387 B2 | 11/2019 | Pigott | |
| 10,485,572 B2 | 11/2019 | Pigott | |
| 10,610,255 B2 | 4/2020 | Pigott | |
| 10,842,971 B2 | 11/2020 | Iwano et al. | |
| 10,874,837 B2 | 12/2020 | Iwano et al. | |
| 2001/0007059 A1 | 7/2001 | Mirzaee | |
| 2002/0010489 A1 | 1/2002 | Grayzel et al. | |
| 2002/0029052 A1 | 3/2002 | Evans et al. | |
| 2002/0143350 A1 | 10/2002 | Heitzmann et al. | |
| 2002/0143362 A1 | 10/2002 | Macovial et al. | |
| 2002/0161394 A1 | 10/2002 | Macoviak et al. | |
| 2003/0069547 A1 | 4/2003 | Gonon | |
| 2003/0125756 A1 | 7/2003 | Shturman et al. | |
| 2003/0144677 A1 | 7/2003 | Lary | |
| 2003/0208215 A1 | 11/2003 | Uflacker | |
| 2004/0034384 A1 | 2/2004 | Fukaya | |
| 2004/0082859 A1* | 4/2004 | Schaer | A61B 18/1492 600/459 |
| 2004/0098014 A1 | 5/2004 | Flugelman | |
| 2004/0122457 A1 | 6/2004 | Weber | |
| 2004/0204738 A1 | 10/2004 | Weber et al. | |
| 2004/0267345 A1 | 12/2004 | Lorenzo et al. | |
| 2005/0055077 A1 | 3/2005 | Marco et al. | |
| 2005/0149102 A1 | 7/2005 | Radisch, Jr. et al. | |
| 2005/0149159 A1 | 7/2005 | Andreas et al. | |
| 2005/0151304 A1 | 7/2005 | Boelens et al. | |
| 2005/0240176 A1 | 10/2005 | Oral et al. | |
| 2006/0020285 A1 | 1/2006 | Niermann | |
| 2006/0089637 A1 | 4/2006 | Werneth et al. | |
| 2006/0111736 A1 | 5/2006 | Kelley | |
| 2006/0116701 A1 | 6/2006 | Crow | |
| 2006/0118127 A1* | 6/2006 | Chinn | A61B 18/04 606/41 |
| 2006/0178695 A1* | 8/2006 | Decant | A61F 2/0105 606/200 |
| 2006/0184191 A1 | 8/2006 | O'Brien | |
| 2006/0253148 A1 | 11/2006 | Leone et al. | |
| 2007/0005093 A1 | 1/2007 | Cox | |
| 2007/0060863 A1 | 3/2007 | Goeken et al. | |
| 2007/0083194 A1 | 4/2007 | Kunis et al. | |
| 2007/0106215 A1 | 5/2007 | Olsen et al. | |
| 2007/0156225 A1 | 7/2007 | George et al. | |
| 2007/0181157 A1 | 8/2007 | Dadourian | |
| 2008/0140051 A1 | 6/2008 | Bei et al. | |
| 2008/0294116 A1 | 11/2008 | Wolter et al. | |
| 2008/0300594 A1 | 12/2008 | Goto | |
| 2008/0300610 A1 | 12/2008 | Chambers | |
| 2009/0099583 A1 | 4/2009 | Butterfield et al. | |
| 2009/0105686 A1 | 4/2009 | Snow et al. | |
| 2009/0192508 A1 | 7/2009 | Laufer et al. | |
| 2009/0204068 A1 | 8/2009 | Nguyen et al. | |
| 2009/0254172 A1 | 10/2009 | Grewe | |
| 2009/0306690 A1 | 12/2009 | Rivers et al. | |
| 2009/0312807 A1 | 12/2009 | Boudreault et al. | |

(56) References Cited

U.S. PATENT DOCUMENTS

| | | |
|---|---|---|
| 2010/0010521 A1 | 1/2010 | Kurrus |
| 2010/0023035 A1 | 1/2010 | Kontos |
| 2010/0076482 A1 | 3/2010 | Shu et al. |
| 2010/0121270 A1 | 5/2010 | Gunday et al. |
| 2010/0168737 A1 | 7/2010 | Grunewald |
| 2010/0168778 A1 | 7/2010 | Braido |
| 2010/0330147 A1 | 12/2010 | Hossainy et al. |
| 2011/0060182 A1 | 3/2011 | Kassab et al. |
| 2011/0152683 A1 | 6/2011 | Gerrans et al. |
| 2011/0160645 A1 | 6/2011 | Sutermeister et al. |
| 2011/0184447 A1 | 7/2011 | Leibowitz et al. |
| 2011/0288479 A1 | 11/2011 | Burton |
| 2012/0053485 A1 | 3/2012 | Bloom |
| 2012/0143054 A1 | 6/2012 | Eaton et al. |
| 2012/0150142 A1 | 6/2012 | Weber et al. |
| 2012/0157988 A1 | 6/2012 | Stone et al. |
| 2012/0172901 A1 | 7/2012 | Manderfeld et al. |
| 2013/0066346 A1 | 3/2013 | Pigott |
| 2013/0116715 A1 | 5/2013 | Weber |
| 2013/0131594 A1 | 5/2013 | Bonnette et al. |
| 2013/0150874 A1 | 6/2013 | Kassab |
| 2013/0237950 A1 | 9/2013 | Gianotti et al. |
| 2013/0253467 A1 | 9/2013 | Gianotti et al. |
| 2014/0121672 A1 | 5/2014 | Folk |
| 2014/0257367 A1 | 9/2014 | Jonsson |
| 2014/0257368 A1 | 9/2014 | Jonsson |
| 2014/0277002 A1 | 9/2014 | Grace |
| 2014/0350523 A1 | 11/2014 | Dehdashtian et al. |
| 2014/0364896 A1 | 12/2014 | Consigny |
| 2014/0371783 A1 | 12/2014 | Shu et al. |
| 2015/0133978 A1 | 5/2015 | Paul, Jr. |
| 2015/0182324 A1 | 7/2015 | Naor et al. |
| 2016/0143721 A1 | 5/2016 | Rosenbluth et al. |
| 2016/0199617 A1* | 7/2016 | Pigott ............ A61B 17/320725 604/533 |
| 2017/0056048 A1 | 3/2017 | Erpen |
| 2017/0238960 A1 | 8/2017 | Hatta et al. |
| 2018/0177985 A1 | 6/2018 | Nakagawa et al. |
| 2020/0289102 A1 | 9/2020 | Wilson et al. |
| 2020/0297376 A1 | 9/2020 | Marks et al. |
| 2021/0023347 A1 | 1/2021 | Iwano et al. |
| 2021/0220008 A1 | 7/2021 | Pigott |

FOREIGN PATENT DOCUMENTS

| | | | |
|---|---|---|---|
| WO | 9502370 | A2 | 1/1995 |
| WO | 1996039997 | A2 | 12/1996 |
| WO | 9918862 | A1 | 4/1999 |
| WO | 02078511 | A2 | 10/2002 |
| WO | 02078511 | A3 | 10/2002 |
| WO | 2007095125 | A2 | 8/2007 |
| WO | 2013159066 | A1 | 10/2013 |
| WO | 2013169596 | A1 | 11/2013 |
| WO | 2014106226 | A2 | 7/2014 |
| WO | 2014142801 | A1 | 9/2014 |
| WO | 2015190578 | A1 | 12/2015 |
| WO | 2015195606 | A1 | 12/2015 |
| WO | 2016210167 | A1 | 12/2016 |

OTHER PUBLICATIONS

Boston Scientific Corporation, FilterWire EZ, Embolic Protection System for Carotid Arteries, Sep. 2015, http://www.bostonscientific.com/en-US/products/embolic-protection/filterwire-ez-embolic-protection-system.html.

International Search Report, Application No. PCT/US2012/055079, dated Jan. 31, 2013.

Boston Scientific, Rotablator Rotational Atherectomy System, http://www.bostonscientific.com/en-US/products/plaque-modification/rotablator-rotational-atherectomy-system.html, 2017.

Covidien, SpiderFX Embolic Protection Device, 2015, https://www.ev3.net/peripheral/US/embolic-protection/spiderfxtrade-embolic-protection-device.htm.

Boston Scientific, Sterling 0.018" Balloon Catheter, Jun. 2015.

Ham, S. et al., Safety of Carbon Dioxide Digital Subtraction Angiography, Archives of Surgery, Dec. 2011.

Alexander, J., CO2 Angiography in Lower Extremity Arterial Disease, Endovascular Today, Sep. 2011, pp. 27-34.

* cited by examiner

INTRAVASCULAR DEVICE HAVING FEEDBACK ELEMENTS

CROSS-REFERENCE TO RELATED APPLICATIONS

This application makes no priority claim.

FIELD OF THE INVENTION

These disclosures relate, in general, to intravascular devices, such as can be used during minimally invasive surgical procedures. In particular, these disclosures relate to an intravascular device having feedback elements.

BACKGROUND AND SUMMARY OF THE INVENTION

Atherosclerosis is a chronic condition in which atheromatous plaque accumulates on the inner walls of a blood vessel. As a result, the blood vessel walls can become inflamed and, over time, may harden to form atherosclerotic lesions that cause a narrowing of the vessel lumen. In severe cases, the atherosclerotic lesions can rupture and induce the formation of thrombus (i.e., blood clots), which can prevent blood flow through the narrowed vessel lumen. Certain such areas can be fully or partially blocked over a distance of the blood vessel. In the case of peripheral artery disease, by way of non-limiting example, these areas tend to be less obstructed (e.g., have a lower level of luminal obstruction) but often have some level of obstruction over a longer length of blood vessel. In other cases, the blockages are relatively severe, but located over a shorter distance.

Fistulas are another example of blood vessels that may become partially or wholly blocked over time. For example, without limitation, AV fistulas are often created for dialysis treatment to provide an access point which may be accessed several times a week without collapsing the vessels. These fistulas may be created from a person's own blood vessels, grafts, or artificial implants, to name a few examples. AV fistulas are known to experience stenosis, which can cause damage to, or failure of, the AV fistula. The mechanism and type of stenosis is generally different from that of certain other blood vessel stenosis (e.g., plaque accumulation). For example, without limitation, the stenosed regions may comprise fibrotic tissue.

There are known procedures and devices for treating or otherwise reducing the risks associated with atherosclerosis or other wholly or partially blocked blood vessels. For example, angioplasty is a procedure in which a balloon catheter is inserted into a narrowed region of the vessel lumen via a delivery catheter. The balloon catheter includes a flexible tube having an inflatable balloon at an end thereof. Once positioned in the narrowed region, the balloon is inflated in order to dilate the narrowed vessel lumen. The pressure in the balloon is generally sufficient to compress the accumulated tissue.

However, certain medical interventions can, in some cases, cause dissection in blood vessels. Dissection may include separation between the plates or layers making up the blood vessel and may occur as a result of the compressive forces exerted against the blood vessel from angioplasty, for example. Low grade dissection is generally considered medically acceptable, but larger grade dissection can have undesirable medical effects.

Certain intravascular devices for scoring atherosclerotic lesions are known. Such devices may be used to fragment atherosclerotic lesions, such to improve luminal gain and/or facilitate fragmentation of the atherosclerotic material during a subsequent angioplasty procedure. Examples of such known devices include those provided in U.S. Pat. No. 9,615,848 issued Apr. 11, 2017, US Pub. No. 2021/0220008 published Jul. 22, 2021, the disclosures of which are hereby incorporated by reference as if fully restated herein (hereinafter collectively also the "Prior Disclosures").

The accumulated tissue in blood vessels does not typically take on a uniform hardness, making controlling and anticipating possible dissection difficult. Some accumulated tissue may be calcified, requiring relatively high pressure for scoring, angioplasty, or other treatment devices to effectuate particular medical effects, such as adequate or desirable luminal gain. Relatively higher pressures may be acceptable in such cases based on the need for the particular medical effect and/or because the pressure is largely transferred to the accumulated tissue rather than the blood vessel or surrounding tissue. Other accumulated tissue may be relatively soft, requiring relatively lower pressure for scoring, angioplasty, or other treatment devices to effectuate the same particular medical effects. Relatively lower pressures may be desirable in such cases because the lower pressures may still provide adequate medical effects and/or because more of the pressure is transferred to the blood vessel wall.

Intravascular devices and systems having feedback elements which, for example without limitation, indicate characteristics of the accumulated tissue (e.g., hardness) and/or forces exerted by the intravascular device (e.g., pressure) are disclosed herein along with methods of utilizing the same. The intravascular devices may comprise some or all of the same or similar components as those provided in the Prior Disclosures, by way of exemplary embodiment without limitation. In exemplary embodiments, without limitation, the intravascular devices may comprise an expandable portion comprising a number of struts configured to be selectively moved between a collapsed position and an expanded position, such as by way of sliding movement of an inner sleeve. The inner sleeve may extend within a catheter tube which extends to a handle assembly, such as within a sheath. The inner sleeve may be connected to a distal end of the struts and/or a tip member at a distal end, and to a control element at the handle assembly at a proximal end. The inner sleeve may accommodate a guide wire. The intravascular devices may alternatively, or additionally, comprise a balloon for moving the struts between the open and closed positions.

One or more feedback devices may be provided at exterior surfaces of said intravascular devices. The feedback devices may comprise devices configured to detect hardness, such as but not limited to durometers, sclerometers, indenters, scleroscopes, pressure sensors, combinations thereof, or the like. Alternatively, or additionally, the feedback devices may comprise devices configured to measure pressure, movement, forces, combinations thereof, or the like, such as but not limited to pressure sensors, strain gauges, accelerometers, combinations thereof, or the like. A single or multiple such feedback devices of the same or different type may be provided at each intravascular device. The feedback devices may be located along one or more struts of the expandable portion in exemplary embodiments.

The feedback devices may be in wired or wireless electronic communication with one or more feedback displays, which may be provided at the intravascular device, or remote therefrom. The feedback displays may be configured to provide feedback data, such as hardness measurements, pressure measurements, force measurements, expansion measurements, combinations thereof, or the like, in substantially real-time or historically from the feedback devices.

For example, without limitation, the feedback devices may be provided on a ring or jacket which surrounds at least part of an outer surface of an expandable portion of the intravascular device. The ring or jacket may surround part or all of an outer surface of a balloon and/or one or more struts forming the expandable portion in exemplary embodiments without limitation. In other exemplary embodiments, without limitation, the feedback devices may be provided along an outer surface of, or integrated with, a balloon or the struts without the need for a separate ring or jacket. While multiple feedback devices are discussed in some places, a single feedback device for each intravascular device may be utilized. Where the intravascular device comprises one or more incising elements, at least one of the feedback devices may, alternatively or additionally, be positioned adjacent to one or more of the incising element(s), and/or at another one of the struts not comprising the incising element, though any location may be utilized. Alternatively, or additionally, feedback devices may be provided at common components which connect multiple ones of the struts, tip members, limiters, combinations thereof, or the like.

The user may monitor the feedback data and adjust expansion of the expandable portion accordingly. For example, without limitation, where harder atherosclerotic material or other tissue is encountered, pressure exerted by the expandable portion may be increased to a relatively higher level. As another example, again without limitation, where softer atherosclerotic material or other tissue is encountered, pressure exerted by the expandable portion may be decreased to a relatively lower level. In other exemplary embodiments, pressure exerted by the expandable portion may be adjusted to one or more benchmarks, thresholds, ranges, or the like which are predetermined to be acceptable or desirable. Such benchmarks, thresholds, ranges, or the like may be those known to result in minimal or acceptable levels of dissection, provide acceptable, desirable, or particular medical effects, combinations thereof, or the like. Such benchmarks, thresholds, ranges, or the like may be specific to hardness levels of the atherosclerotic material, the tissue encountered, the location of the treatment area, combinations thereof, or the like, though such is not required. In this way, chances of dissection or other undesirable effects may be minimized.

Expansion of the expandable portion may be accomplished by way of one or more control devices, which may be located on a handle subassembly of the intravascular devices, though such is not required. Adjustments to the control member may be accomplished manually by the user or may be automatic, such as based on one or more criteria set by the user. For example, without limitation, the one or more control devices may be configured to accept user input regarding desired expansion of the expandable portion, exertion of a particular pressure, treatment of a particular type, location, and/or kind of atherosclerotic material or other tissue (e.g., by hardness level, tissue type), location of treatment area, patient information (e.g., age, weight, risk factors, etc.), combinations thereof, or the like.

Various aspects of this invention will become apparent to those skilled in the art from the following detailed description of the preferred embodiments, when read in light of the accompanying drawings.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF THE PREFERRED EMBODIMENTS

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
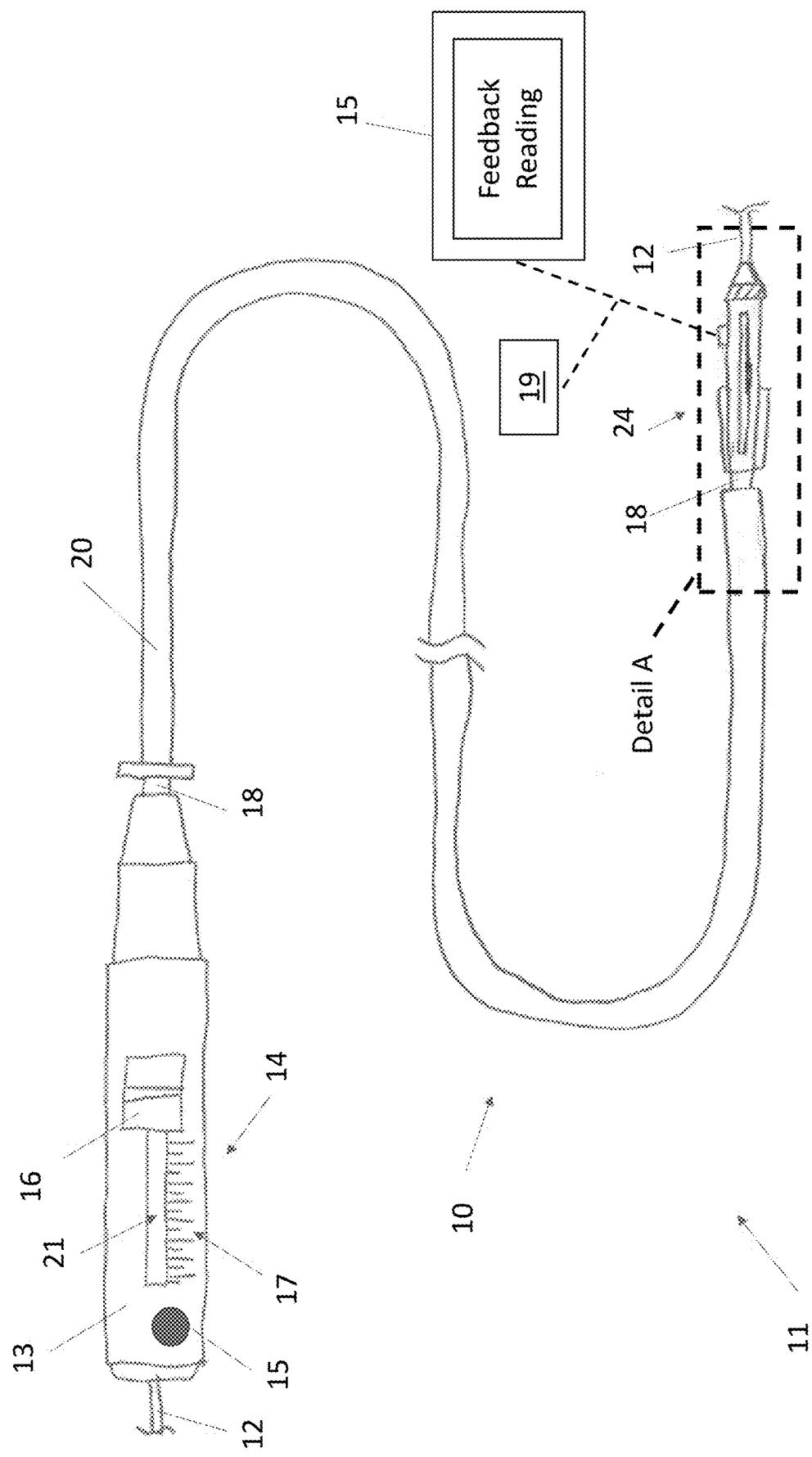
FIG. 1 is plan view of an exemplary intravascular device with feedback elements and related system, also indicating detail A.

FIG. 1 illustrates a system 11 comprising an intravascular device 10 with feedback elements 34. The intravascular device 10 may comprise some or all of the components of the Prior Disclosures, the contents of which are hereby incorporated by reference as if fully restated herein.

The intravascular device 10 may comprise a handle subassembly 14. The handle subassembly 14 may comprise a housing 13. The handle subassembly 14 may be configured to accommodate a guide wire 12 passing through some or all of the handle subassembly 14.

The handle subassembly 14 may comprise one or more control elements 16. The control element(s) 16 in exemplary embodiments, without limitation, may comprise one or more levers, sliders, dials, knobs, buttons, motors, relays, touch pads, electronic controls, combinations thereof, or the like which are moveable or otherwise actuatable to operate an expandable portion 24 or other components of the device 10.

A catheter tube 18 may extend from the handle subassembly 14 to the expandable portion 24. The catheter tube 18 may be attached to, or extend within, the handle assembly 14.

A sheath 20 may be provided, though such is not necessarily required. Some or all of the catheter tube 18 may extend through the sheath 20. The sheath 20 may be connected to the handle subassembly 14 or be separate therefrom.

An inner sleeve 26 may extend within the catheter tube 18. The inner sleeve 26 may be configured for sliding movement within the catheter tube 18. The inner sleeve 26 may be connected, directly or indirectly, to one or more of the control element(s) 16, in exemplary embodiments without limitation, such that sliding or other actuation of the control element(s) 16 is translated to corresponding movement of the inner sleeve 26.

The catheter tube 18, the inner sleeve 26, the sheath 20, and/or the guide wire 12 may comprise sufficiently flexible material to permit navigation of sinuous blood vessel within a patient's vascular system. The inner sleeve 26 may comprise a tube or other hollow member, though in other exemplary embodiments the inner sleeve 26 may comprise one or more solid members of any size or shape, such as but not limited to a wire, pushrod, linkage, combinations thereof, or the like. In exemplary embodiments, without limitation, the entire inner sleeve 26 and at least a portion of the handle subassembly 14 may be configured to accommodate the guide wire 12. In other exemplary embodiments, only the expandable portion 24, or a portion thereof, may be configured to accommodate the guide wire 12. For example, without limitation, a distal portion of the inner sleeve 26 may comprise one or more holes, slits, or the like for allowing the guide wire 12 to enter and exit a portion of the expandable portion 24.

One or more indicators 17 may be provided, such as at the handle subassembly 14, for indicating status of the expandable portion 24. The indicators 17 may comprise marking on the housing 13 (e.g., for marking location of one or more of the control element(s) 16 relative to the housing), electronic displays, gauge, lights, combinations thereof, or the like.

Figure 2:
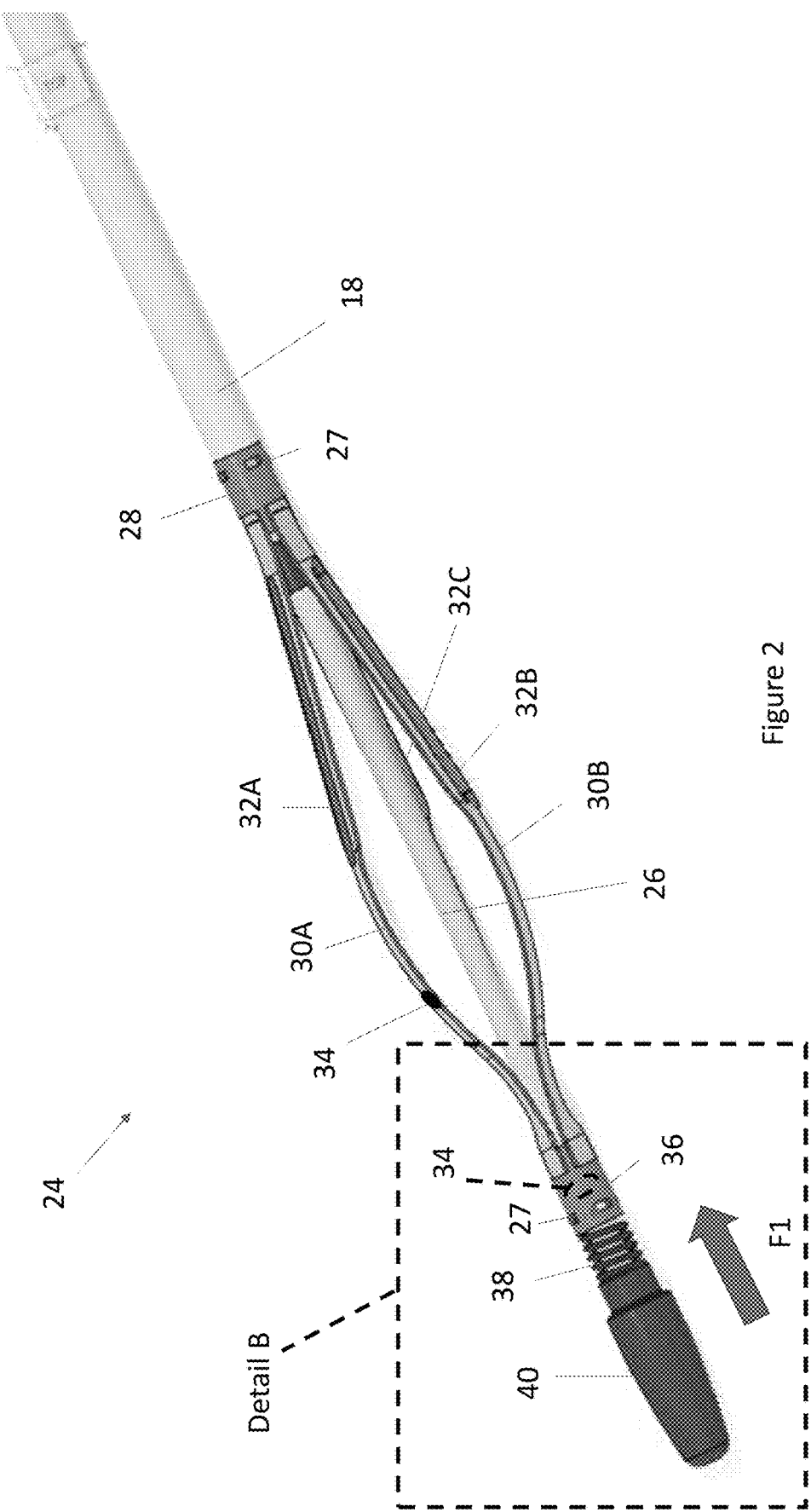
FIG. 2 is a detailed perspective view of an exemplary embodiment of an expandable portion of detail A of FIG. 1, also indicating detail B.
Figure 3:
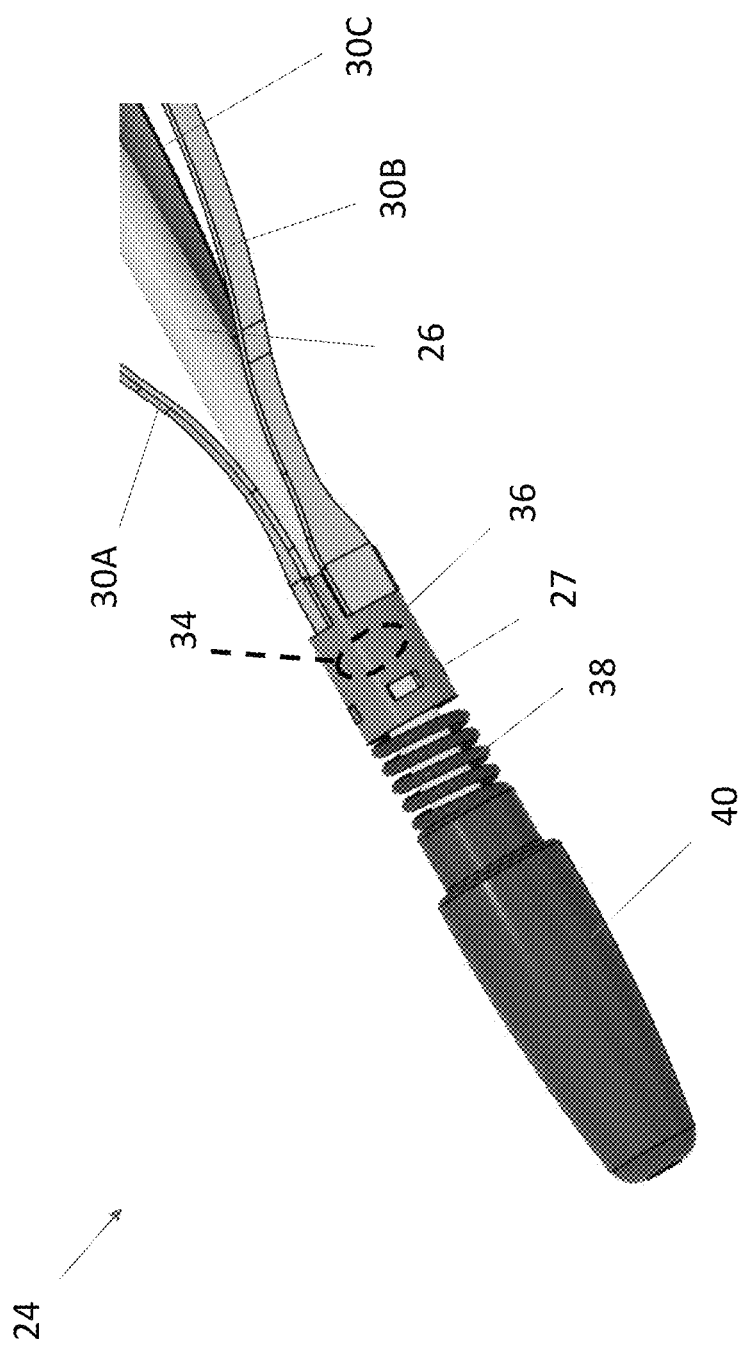
FIG. 3 is a detailed perspective view of detail B of FIG. 2.
Figure 4:
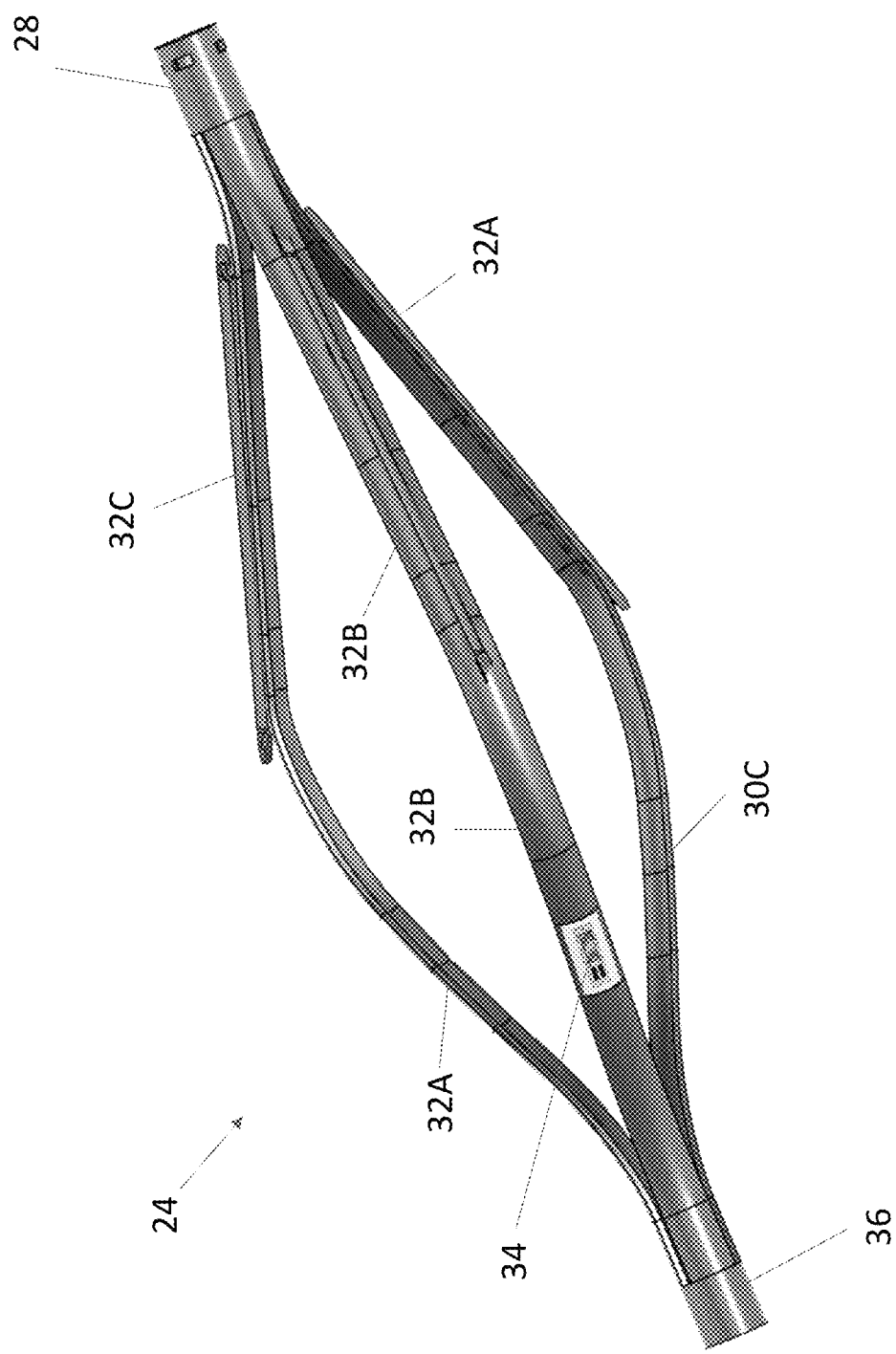
FIG. 4 is a detailed perspective view of another exemplary embodiment of an expandable portion of detail A of FIG. 1 with certain components not illustrated for clarity.

Referring additionally to FIG. 2 through FIG. 4, the expandable portion 24 may comprise one or more struts 30. In exemplary embodiments, without limitation, the expandable portion 24 comprises three struts 30A, 30B, 30C. The struts 30A, 30B, 30C may be provided substantially equidistant about the inner sleeve 26. Any number of struts 30 in any arrangement may be utilized. The struts 30, in exemplary embodiments without limitation, may each comprise a longitudinal axis that extends along a longitudinal axis of the expandable portion 24. The struts 30 may extend along a longitudinal axis of at least an adjacent portion of the guide wire 12, the inner sleeve 26, the catheter tube 18, and/or the sheath 20 in exemplary embodiments without limitation. The struts 30 in exemplary embodiments, without limitation, may comprise a flattened outer surface. For example, without limitation, the struts 30 may comprise an oval or rectangular shaped cross section, though any size, shape, or kind of struts 30 may be utilized. This may permit the outer surfaces of the struts 30 to ride along tissue within the blood vessel and/or the blood vessel wall.

The expandable portion 24 may comprise a first common attachment component 28 and/or a second common attachment component 36. The struts 30 may be attached to the first common attachment component 28 at a first end thereof, and/or the second common attachment component 36 at a second end thereof. The inner sleeve 26 may be connected to the second common attachment component 36 in exemplary embodiments, without limitation. The first common attachment component 28 may be affixed to a distal end of the catheter tube 18 in exemplary embodiments. As the inner sleeve 26 may be configured for sliding movement while the catheter tube 18 remains relatively fixed, the struts 30 may be configured to bow outwardly upon retraction of the inner sleeve 26 in exemplary embodiments, such as a result of compressive force(s) F1 exerted against the struts 30. In exemplary embodiments, without limitation, the control element(s) 16 may comprise a slider which is operable for sliding movement within a slot 21 on the handle subassembly 14 to cause direct, translational sliding movement of the inner sleeve 26 within the catheter tube 18 to provide the compressive force(s) F1 and resulting movement of the struts 30 into an expanded position. In the expanded position (see e.g., FIGS. 2-5), a mid-portion of the struts 30 may bow outwardly away from the inner sleeve 26 such that the expandable portion 24 defines a maximum outer diameter, which is larger than a maximum outer diameter of the expandable portion 24 when in a collapsed position (see e.g., FIG. 1) where the struts 30 rest on, or extend along (such as but not limited to substantially parallel to) but are spaced apart from, the inner sleeve 26.

The first common attachment component 28, the second common attachment component 36, and/or the struts 30 may be integrally formed in exemplary embodiments. For example, without limitation, the first common attachment component 28, the second common attachment component 36, and/or the struts 30 may be formed in a sheet of material. Elongated slits may be formed, such as by punching, cutting, combinations thereof, or the like, into the sheet of material to form the struts 30 and/or the first and/or second common attachment components 28, 36 and rolled. Multiple such slits may be provided to form multiple struts 30A, 30B. Any number of slits and accompanying struts 30 may be formed at any arrangement or spacing. Some or all of the expandable portion 24 may be formed and/or assembled as provided in the Prior Disclosures.

The inner sleeve 26 may comprise components, such as but not limited to protrusions, configured to interact with components, such as but not limited to apertures 27, at the first common attachment component 28. Alternatively, or additionally, the catheter tube 18 may comprise components, such as but not limited to protrusions, configured to interact with components, such as but not limited to apertures 27, at the second common attachment component 36. Any number, size, shape, arrangement, or the like of such apertures 27 may be utilized.

In other exemplary embodiments, without limitation, the struts 30 may be joined to the first and/or second common attachment components 28, 36, such as by adhesive, welding, combinations thereof, or the like. The first and/or second common attachment components 28, 36 may be attached to the catheter tube 18 and the inner sleeve 26, respectively such as by protrusions on the catheter tube 18 and the inner sleeve 26 which frictionally engage with holes 27 in the first and/or second common attachment components 28, 36, respectively. Alternatively, or additionally, the first and/or second common attachment components 28, 36 may be attached to the catheter tube 18 and the inner sleeve 26 by adhesive, welding, combinations thereof, or the like.

The struts 30 may comprise one or more resiliently deformable materials such that the struts 30 are biased in the collapsed position, though such is not required. Alternatively, the struts 30 may be biased in the expanded position such that they are automatically expanded upon removal from the sheath 20. The struts 30 may comprise material which permits flexibility in bending to form an arch or other curve shape and bow outward. Alternatively, or additionally, the struts 30 may comprise one or more weakened regions, hinging areas, or the like which permit sections of the struts 30 to remain relatively non-deformed, at least along sections thereof. In this manner, proximal, medial, and/or distal portions of the struts 30 may form a relatively linear outer surface.

A tip member 40 may be provided. The tip member 40 may be connected to the second common connection component 36 and/or the inner sleeve 26. For example, the tip member 40 may be attached to the inner sleeve 26 at a position spaced apart from the second common connection component 36.

A limiter 38 may be provide between the second common connection component 36 and the tip member 40. Alternatively, the limiter 38 may be provided between the struts 30 and the tip member 40. The limiter 38 may be configured to cause the struts 30 to expand only to a predetermined size when placed in the expanded position. The limiter 38 may comprise one or more springs configured to provide sufficient forces (e.g., F1) axially along said inner sleeve 26 and/or catheter tube 18 towards said handle assembly 14 to force said struts 30 to bow outwardly when said struts 30 are exposed form the sheath 20 for expansion into the expanded position. In this way, the limiter 38 may act to bias the expandable portion 24 in the expanded position. Because the amount of force applied by the limiter 38 may be predetermined and/or limited, this may prevent the struts 30, and attached tissue modification elements 32, from expanding beyond a desired diameter and/or providing more forces or pressure than desired. This arrangement may permit retraction of the sheath 20 beyond the expandable portion 24 without necessarily changing the size of the expandable portion 24 and/or the forces exerted by the tissue modification elements 32. This may be particularly advantageous where the otherwise tortuous nature of the vascular system and/or other characteristics of the access site may make precise control of the size of the expandable portion 24, such as by movement of the control element(s) 16 difficult. This may also prevent over expansion of the expandable portion 24 and/or over exertion of forces at the tissue modification elements 32. The limiter 38 is not required. The tip member 40 may be configured to accommodate the guide wire 12.

In other exemplary embodiments, without limitation, the tip member 40 is located along the inner sleeve 26 at an area proximal to a proximal end of the struts 30, and the proximal end of the struts 30 are free such that the struts 30 are forced for bow outwardly as the tip member 40 is retracted along interior surfaces of the struts 30, such as in a cantilevered fashion. In such embodiments, a second end of the struts 30 may be free, such that the second common connection component 36 is not required. The struts 30 in such embodiments may be configured for cantilevered operation such as provided in the Prior Disclosures.

The sheath 20, in exemplary embodiments without limitation, may be configured for sliding movement so as to selectively expose, or cover, the expandable portion 24. One or more control element(s) 16 may be provided on the handle subassembly 14 for moving the sheath 20, though such is not required. For example, without limitation, the sheath 20 may be manually slidable. In other exemplary embodiments, without limitation, the sheath 20 may be fixed, and the expandable portion 24 may be moveable relative to the sheath 20.

Some or all of the struts 30 may comprise one or more of the tissue modification elements 32. Each of the tissue modification elements 32 may comprise a protrusion, blade, sharpened edge, blunted edge, combination thereof, or the like which extends from an outer surface of a respective one of the struts 30. Each of the tissue modification element 32 may extend along a longitudinal axis of the respective one of the struts 30 to which it is attached or forms part of. Each of the tissue modification elements 32 may extend along a longitudinal axis of the expandable portion 24. Each of the tissue modification elements 32 may extend along some, or all, of the respective one of the struts 30 which it is provided on. In exemplary embodiments, without limitation, the tissue modification elements 32 may extend along a proximal portion of the struts 30, such as but not limited to along substantially half, or less than half, of the struts 30. Each of the tissue modification elements 32 may comprise an arcuate element, a blunted cuboid protrusion, a triangular prism, combinations thereof, or the like to name a few examples without limitation. Any size, shape, or type of the tissue modification elements 32 may be utilized to score, incise, cut, remove, or otherwise modify atherosclerotic material or other tissue or elements at a blood vessel or other treatment area.

The intravascular device 10 may comprise one or more feedback devices 34. The feedback devices 34 may comprise one or more pressure sensors, hardness sensors, strain gauges, combinations thereof, or the like. One or more such feedback device 34 may be provided at exterior surfaces of said intravascular device 10, such as but not limited to along a portion of one or more of the struts 30. For example, without limitation, a feedback device 34 may be provided along a forward portion of a strut 30, at middle portion thereof, a proximal portion thereof, combinations thereof, or the like. The feedback devices 34 located along the strut(s) 30 may comprise hardness sensors for detecting hardness of surrounding tissue, pressure sensors for detecting pressure applied by strut(s) 30, strain gauges to measure strut 30 deflection, combinations thereof, or the like.

Alternatively, or additionally, one or more such feedback devices 34 may be provided at or between the second common attachment component 36, the limiter 38, and or the tip member 40. In this manner, the forces F1 provided, for example, may be determined.

A single or multiple such feedback devices 34 of the same or different type may be provided at some or all components of the expandable portion 24 to measure the same or different data points.

In exemplary embodiments, without limitation, the feedback device(s) 34 may comprise one or more strain gauges provided at one or more of the struts 30. The strain gauge(s) may be configured to measure strut 30 deflection, for example without limitation. For example, without limitation, the stain gauge(s) may be configured to measure localized deflection of a portion of an associated one of the struts 30. Alternatively, or additionally, the strain gauge(s) may be configured to measure forces exerted by the strut(s) 30 to the surrounding tissue. The strain measurements may be used to determine a level of resistance met at the tissue in exemplary embodiments, without limitation. This may reflect tissue hardness, operator force provided, luminal gain achieved, combinations thereof, or the like.

Alternatively, or additionally, the feedback device(s) 34 may comprise one or more pressure sensors. For example, the pressure sensor(s) may be provided at one or more of the struts 30 and may be configured to measure pressure exerted between one or more of the struts 30 and the tissue. As another example, without limitation, the pressure sensors may be located at, or between, the tip member 40, the limiter 38, and/or the second common attachment component 36, to measure compressive forces exerted to the struts 30. Regardless, the pressure measurements may be used to determine operator force, resistance encountered, luminal gain achieved, combinations thereof, or the like by way of non-limiting example. In exemplary embodiments, the pressure sensor(s) of the feedback device(s) may be attached to, or otherwise connected with, a spring or other component of the limiter 38.

Alternatively, or additionally still, the feedback device(s) 34 may comprise hardness sensors configured to measure hardness of the surrounding tissue. Such hardness sensors may include, for example without limitation, durometers, sclerometers, indenters, scleroscopes, pressure sensors, combinations thereof, or the like. Any type or kind of sensor, or combination of sensors, for measuring hardness of material, particularly that of human tissue, may be utilized.

Feedback data from the feedback device(s) 34 may be provided quantitively in raw form and/or qualitatively and/or quantitively as an associated exerted pressure, measure of expansion of the expandable portion 24, resistance encountered, operator force provided (e.g., at the expandable portion 24), luminal gain achieved, combinations thereof or the like. Such translational measurements may be made by way of one or more controller(s) 19 in exemplary embodiments. For example, without limitation, the controller(s) 19 may be configured to translate a raw measurement into a readable number and/or a graphical display approximating the reading relative to one or more benchmarks (e.g., graph, dial, gauge, bar chart, color coded, combinations thereof, or the like).

Figure 5:
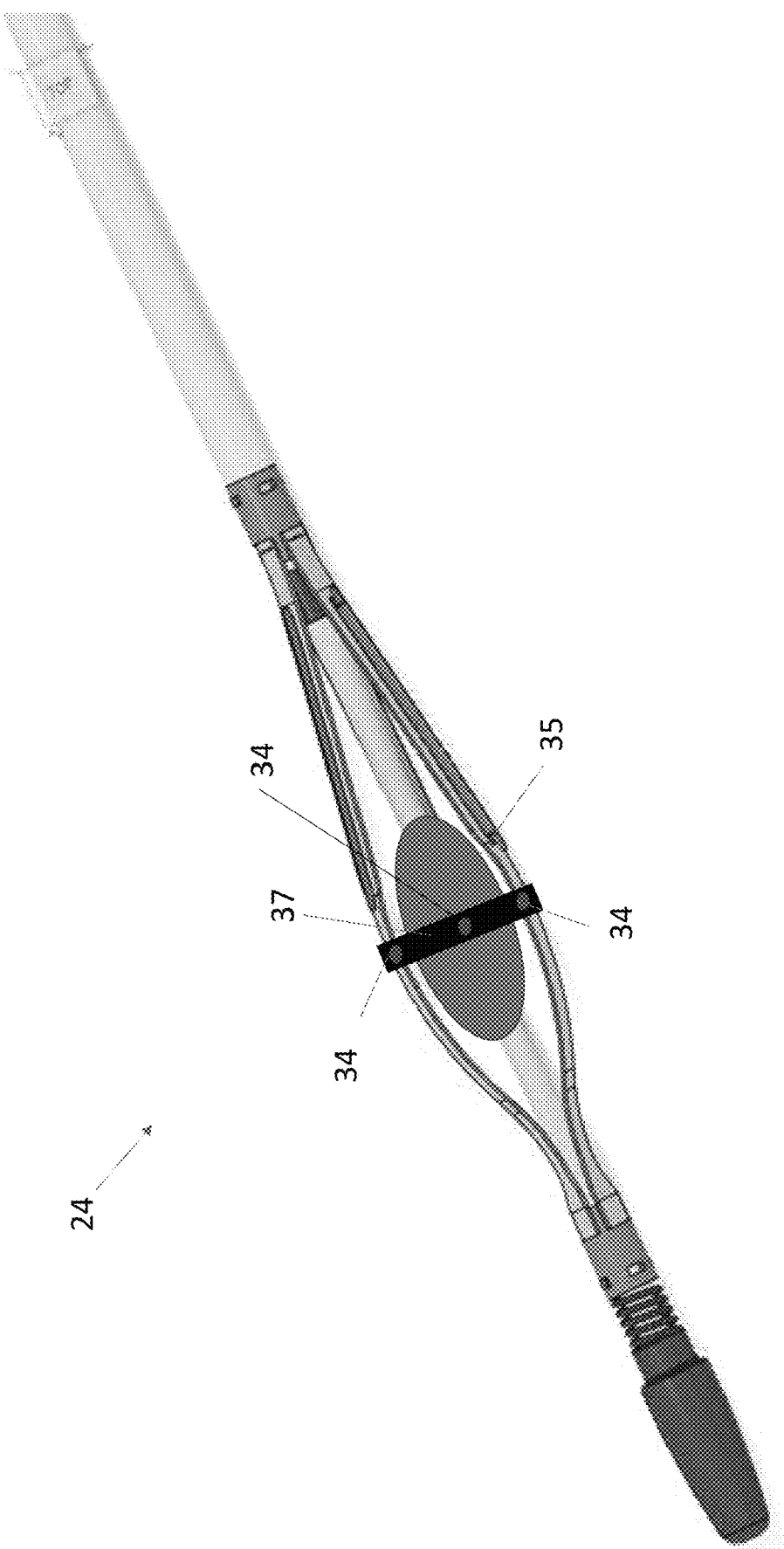
FIG. 5 is a detailed perspective view of another exemplary embodiment of an expandable portion of detail A of FIG. 1.

As illustrated in FIG. 5, one or more balloons 35 may be used as an alternative to, or addition to, the inner sleeve 26 for controlling movement of the struts 30. The balloon(s) 35 may be in fluid communication with a pump, reservoir, or compressed air source, combinations thereof, or the like at the handle subassembly 14 or outside thereof for providing inflation fluid to the balloon(s) 35. Fluid communication may be accomplished, in exemplary embodiments, by way of the catheter tube 18, the inner sleeve 26, and/or one or more tubes extending within the same. In such embodiments, the balloon(s) 35 may be inflated to about 1 atmosphere to 10 atmospheres. The inner sleeve 26 in such embodiments may be moveable, or fixed, such as to provide support to the balloon(s) 35. Alternatively, the inner sleeve 26 may not be utilized in such embodiments.

The feedback devices 34 may be provided on a ring or jacket 37 which may surround at least part of an outer surface of an expandable portion 24 of the intravascular device 10. The ring or jacket 34 may surround part or all of an outer surface of a balloon 35 and/or one or more struts 30 in exemplary embodiments without limitation. In other exemplary embodiments, without limitation, the feedback devices may be provided along an outer surface of, or integrated with, the balloon 35 or the struts 30 without the need for a separate ring or jacket 37.

Figure 6:
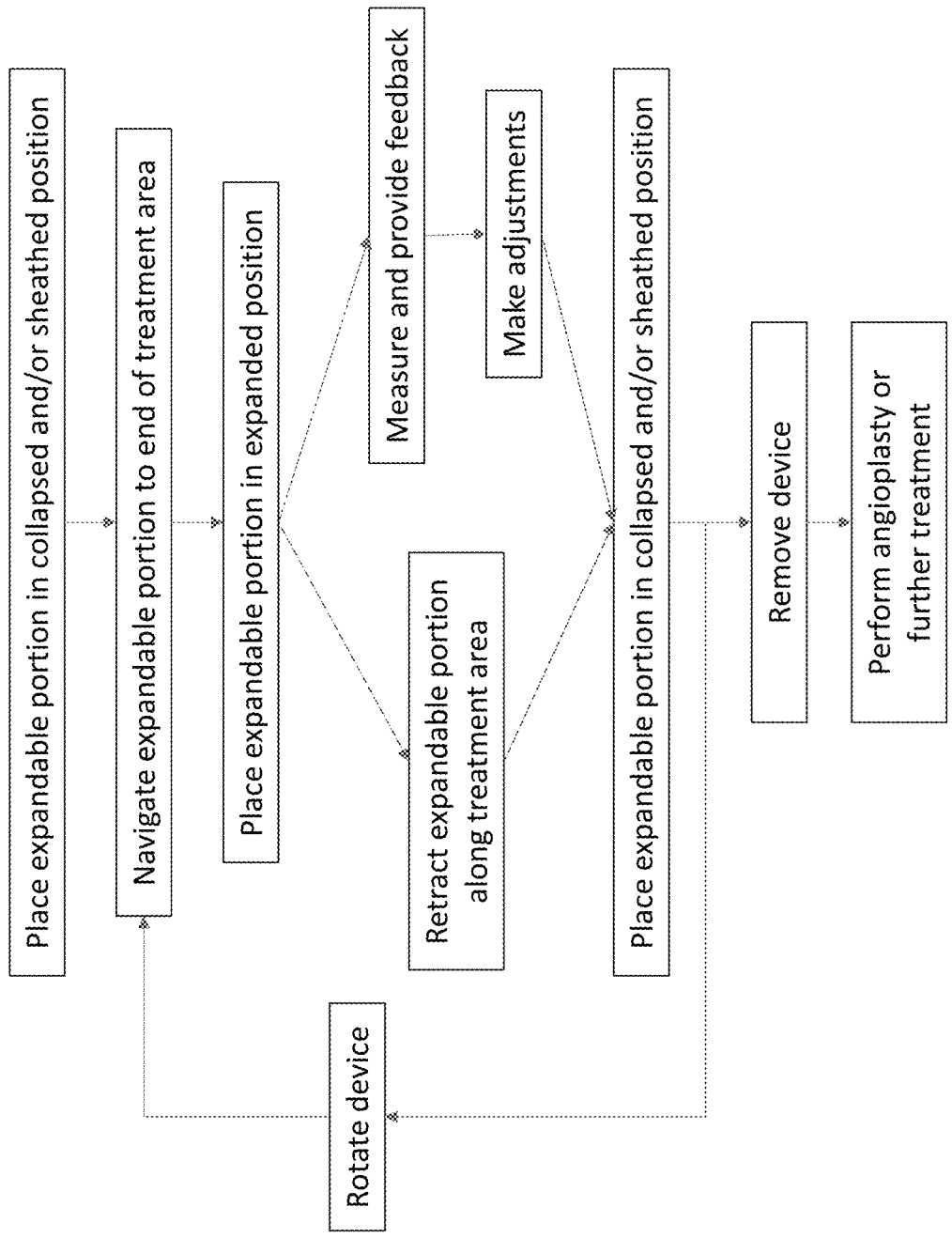
FIG. 6 is a flow chart with an exemplary method for using the system and devices of FIGS. 1-5.

Referring additionally to FIG. 6, in exemplary embodiments, without limitation, the guide wire 12 may be introduced to the patient's vascular system and advanced to a treatment area. The guide wire 12 may be advanced to a distal end of the treatment area, or beyond to give room for maneuvering. Part of the device 10, such as the expandable portion 24, may be introduced to the patient's vascular system in the collapsed and/or sheathed state and advanced in the collapsed and/or sheathed state to a treatment area, such as an area of stenosis (e.g., plaque or other tissue accumulation) within a blood vessel. The treatment area may be a peripheral artery or fistula, for example without limitation—any location, or multiple locations, within the patient's vascular system may be treated. In exemplary embodiments, part of the device 10, such as the expandable portion 24, may be advanced along the guide wire 12. For example, without limitation, the expandable portion 24 may be manually fed over the guide wire 12 which may extend through the inner sleeve 26 and out the handle subassembly 14. Alternatively, or additionally, a distal portion of the inner sleeve 26 may comprise one or more holes, slits, or the like for allowing the guide wire 12 to enter and exit a portion of the expandable portion 24 without necessarily extending through all of the inner sleeve 26 and/or the handle subassembly 14.

The expandable portion 24 may be unsheathed and/or placed in the expanded position at an end of the treatment area and moved along the treatment area. The expandable portion 24 may be moved along the guide wire 12 extending therethrough. The expandable portion 24, and particularly the tissue modification elements 32, may modify the plaque or other tissue, such as by scoring, as the expandable portion 24 is retracted along the treatment area. The expandable portion 24 may be initially positioned at a distal end of the treatment area and retracted therethrough, such as along the guide wire 12, while in the expanded position to score tissue located therein. This may permit movement of the expandable portion 24 counter to natural blood flow, though such is not required. Scoring may include creation of axially extending slits in the plaque or other tissue. Doing so may break surface tension in the plaque or other tissue, resulting in luminal gain by itself and/or in combination with subsequent angioplasty, such as performed by a separate device at the treatment area once the expandable portion 24 is removed. Subsequent angioplasty is not required. Other treatments may also be simultaneously or subsequently performed, including but not limited to, imaging, stenting, medication delivery, combinations thereof, or the like. In exemplary embodiments, without limitation, the outer surface of the struts 30 may ride along the plaque or other tissue, such as while the expandable portion 24 is retracted. This may limit a penetrative depth of the tissue modification elements 32 into the plaque or other tissue.

The tissue modification elements 32 may be coated with one or more medications, in exemplary embodiments, without limitation. In this manner, medication may be delivered at the time of incision.

Multiple passes of the expandable portion 24 may be made, though a single pass may be utilized. The expandable portion 24 may be rotated between such passes to create additional slits, incisions, or other modifications to the plaque or other tissue. Such rotation may be performed at various times, including before repositioning the expandable portion 24 at the distal end of the treatment area, after repositioning the expandable portion 24 at the distal end of the treatment area, while repositioning the expandable portion 24 at the distal end of the treatment area, while retracting the expandable portion 24, combinations thereof, or the like. The expandable portion 24 need not be repositioned at the same start or end point for each retraction pass. Multiple passes may be made without rotation, such as to create deeper slits, wider slits, additional slits in close proximity, break through harder tissue, with different pressures or forces applied, different levels of expansion provided at the expandable portion 24, combinations thereof, or the like. Other types or kinds of tissue modifications may be achieved, such as with different size and/or shape tissue modification elements 32.

The feedback devices 34 may be in electronic communication with one or more feedback displays 15. Such electronic communication may be made by way of wired and/or wireless connections. Wires, near field communication devices, network connectivity devices, wireless routers, combinations thereof, or the like may be provided at the intravascular device 10, the feedback display 15, and/or interim components (e.g., servers, gateways, routers, remote devices, processors, controllers, etc.) for accomplishing the wired or wireless connection. Wires may be extended within or along the inner sleeve 26, catheter tube 18, sheath 20, combinations thereof, or the like in exemplary embodiments. Alternatively, or additionally, a wireless transmitter/receiver may be located at the expandable portion 24 for wireless communication.

The feedback displays 15 may be provided at the intravascular device 10, such as but not limited to, integrated with the handle subassembly 14, or at separate devices. The feedback display 15 may comprise electronic displays, gauge, dials, combinations thereof, or the like. The separate devices may comprise, but are not limited to, dedicated displays, computers, smartphone, tablets, smartwatches, combinations thereof, or the like. The feedback displays 15 may be configured to provide feedback data in substantially real-time or later. Such feedback data may comprise hardness and/or pressure readings from the feedback devices 34 by way of non-limiting example. The feedback data provided may be qualitative or quantitative, such as in absolute measure, relative measure, combinations thereof, or the like.

A user may monitor the feedback data provided at the feedback display 15 and adjust expansion of the expandable portion 24 accordingly. For example, without limitation, where harder atherosclerotic material is encountered, pressure exerted by the expandable portion 24 may be increased to a relatively higher level. As another example, again without limitation, where softer atherosclerotic material is encountered, pressure exerted by the expandable portion 24 may be decreased to a relatively lower level. In such embodiments, one or both or hardness, pressure, and/or strut 30 deflection may be measured and monitored, for example. In other exemplary embodiments, pressure exerted by the expandable portion 24 and/or deflection of the struts 30 may be adjusted to one or more benchmarks, thresholds, ranges, or the like. Such benchmarks, thresholds, ranges, or the like may be those known to result in minimal or acceptable levels of dissection, provide acceptable, desirable, or particular medical effects, combinations thereof, or the like. Such benchmarks, thresholds, ranges, or the like may be specific to hardness levels of the atherosclerotic material or not. In this way, chances of dissection may be minimized. Such benchmarks, thresholds, ranges, or the like may be provided at the feedback display 15, such as by way of one or more controllers 19 and/or in comparison with actual provided pressures. The control element(s) 16 in exemplary embodiments, without limitation, may be manually or automatically, such as by the controller 19, adjusted based on actual readings from the feedback device(s) 34 relative to such benchmarks, thresholds, ranges, or the like. The controller(s) 19 may be remote from the intravascular device 10 and/or integrated therewith.

While multiple feedback devices 34 are discussed in some places, a single feedback device for each intravascular device may be utilized of a same or different type. Where the intravascular device comprises one or more tissue modification elements 32, at least one of the feedback devices 34 may be positioned adjacent to one or more of the tissue modification elements 32, or on another strut 30 not comprising the tissue modification element 32, though any location may be utilized. Where multiple feedback devices 34 are utilized, the controller 19 may be configured to display multiple data points (e.g., one for each feedback device 34), provide an average reading, maximum reading, minimum reading, median reading, mode reading, combinations thereof, or the like.

After completing treatment, the expandable portion 24 may be removed from the treatment area and/or from the patient. Angioplasty may subsequently be performed, such as by way of one or more separate devices, though such is not required. Alternatively, or additionally, stents or other devices may be placed to help maintain the achieved luminal gains or other medical results. Such stents or other devices may be placed by the device 10, angioplasty device, or other device.

The struts 30, the tissue modification elements 32, and/or the balloon 35 may be coated with one or more materials, though such is not required. Such materials may comprise lubricious and/or medicated coatings in exemplary embodiments, without limitation.

Components of the device 10 may comprise one or more materials such as, but not limited to, one or more metals (e.g., nickel titanium alloy), polymers, combinations thereof, or the like. Materials utilized may be biocompatible, sterilizable, combinations thereof, or the like. Components of the device 10 may be integrally formed or joined, such as by welding, brazing, adhesion, mechanical fasteners, combinations thereof or the like.

While sometimes described as being used for treating plaque in blood vessels, such as sometimes results from peripheral artery disease, the system 11 and/or device 10 may be used to treat any type of kind of tissue in any location, such as but not limited to other bodily tissue within a patient's vascular system. For example, without limitation, the system 11 and/or device 10 may be used to treat stenosed areas of fistulas.

Any embodiment of the present invention may include any of the features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention.

Certain operations described herein may be performed by one or more electronic devices. Each electronic device may comprise one or more processors, electronic storage devices, executable software instructions, combinations thereof, and the like configured to perform the operations described herein. The electronic devices may be general purpose computers or specialized computing devices. The electronic devices may comprise personal computers, smartphone, tablets, databases, servers, or the like. The electronic connections and transmissions described herein may be accomplished by wired or wireless means. The computerized hardware, software, components, systems, steps, methods, and/or processes described herein may serve to improve the speed of the computerized hardware, software, systems, steps, methods, and/or processes described herein.

What is claimed is:

1. An intravascular device for providing feedback to an operator during use, said intravascular device comprising:
a handle assembly;
a control element located at said handle assembly;

a catheter tube extending from said handle assembly;
an expandable portion connected to said catheter tube and comprising a first common attachment component, a second common attachment component, and a plurality of struts, each extending between the first common attachment component and the second common attachment component, wherein said expandable portion is selectively movable between a first position and an expanded position where the struts bow outwardly, and wherein the longitudinal axis of each of the struts extends along a longitudinal axis of the expandable portion when said expandable portion is in the first position;
an incising element an outer surface of one for the plurality of struts and having a longitudinal axis extending along a longitudinal axis of a respective one of the struts;
an inner sleeve attached to said control element at a first end, wherein sliding movement of said inner sleeve within said catheter tube moves said expandable portion between said first position and said expanded position;
a lip member connected to said inner sleeve and configured to accommodate a guide wire:
a limiter interposed between said second attachment point and said tip member; and
one or more feedback devices comprising at least one hardness sensor provided at a mid-portion of an outer surface of said expandable portion and at least one pressure sensor connected to said limiter.

2. The intravascular device of claim 1 wherein:
said one or more feedback devices comprises a strain gauge.

3. The intravascular device of claim 1 wherein:
said expandable portion comprises a balloon.

4. The intravascular device of claim 3 wherein:
said feedback device comprises multiple sensors placed about a circumference of the balloon.

5. The intravascular device of claim 4 further comprising:
a jacket provided circumferentially about a midline of said balloon and configured for expansion with the balloon, wherein said multiple sensors are spaced apart along said jacket.

6. The intravascular device of claim 1 further comprising:
a feedback display;
a controller electronically interposed between said feedback device and said feedback display, wherein controller is configured to cause information to be displayed at said feedback display in accordance with data received from said feedback device.

7. A method for providing feedback while operating the intravascular device of claim 1 within a person's vascular system, said method comprising the steps of:
placing the expandable portion in the first position;
navigating the expandable portion to a treatment area of a blood vessel forming part of the person's vascular system;
placing the expandable portion in the expanded position such that the incising element contacts tissue located along a wall of the blood vessel at the treatment area;
retracting the expandable portion along the treatment area to create axially extending incisions in said tissue; and
while retracting the expandable portion along the treatment area:
receiving feedback data from the feedback device; and
displaying indications of said feedback data at a feedback display visible to an operator of said intravascular device.

8. The method of claim 7 wherein:
said feedback device comprises at least one strain gauge provided at an outer surface of at least one of the struts; and
said feedback data comprises readings from said at least one strain gauge.

9. The method of claim 7 wherein:
said feedback data comprises pressure readings from said at least one pressure sensor and hardness readings from said at least one hardness sensor.

10. The method of claim 9 wherein:
said at least one hardness sensor is selected from the group consisting of: durometers, sclerometers, indenters, scleroscopes, and pressure sensors.

11. The method of claim 7 wherein:
said feedback data is provided in substantially real time.

12. An intravascular device for providing feedback to an operator during use, said intravascular device comprising:
a handle assembly;
a catheter tube extending from said handle assembly;
an expandable portion comprising struts extending between a first common attachment component connected to said catheter tube and a second common attachment component, wherein said expandable portion is selectively movable between a first position and an expanded position whereby said struts are moved outward;
an inner sleeve extending within the expandable portion, said inner sleeve configured to accommodate a guide wire;
a tip member located distal to the expandable portion along the inner sleeve and configured to accommodate the guide wire;
a feedback device provided at said expandable portion; and
a limiter interposed between said second common attachment component of said expandable portion and said tip member.

13. The intravascular device of claim 12 further comprising:
a control element located at the handle assembly, wherein said inner sleeve is attached to said control element at a first end, and said expandable portion at a second end, and wherein movement of said control element is configured to cause sliding movement of said inner sleeve within said catheter tube to move said expandable portion between said first position and said expanded position.

14. The intravascular device of claim 13 wherein:
said feedback device comprises a pressure sensor; and
said pressure sensor is connected to said limiter.

15. An intravascular device for providing feedback to an operator during use, said intravascular device comprising:
a handle assembly;
a catheter tube extending from said handle assembly;
an expandable portion connected to said catheter tube, said expandable portion comprising a balloon which is selectively inflatable for moving said expandable portion between a first position and an expanded position;
a jacket provided circumferentially about a midline of said balloon and configured for expansion with the balloon; and
harness and/or pressure sensors spaced apart along said jacket.

16. The intravascular device of claim 15 wherein:
the expandable portion further comprises struts; and
the balloon is located within the struts.

17. The intravascular device of claim 16 further comprising:
- a fluid passageway located within the catheter tube and fluidly connected to the balloon for receiving inflation fluid for moving the balloon into the expanded position.

18. The intravascular device of claim 17 further comprising:
- a tip member spaced apart from a distal end of the second common attachment component; and
- a limiter interposed between the distal end of the second common attachment component and a proximal end of the tip member.

19. The intravascular device of claim 16 wherein:
each of the struts has a longitudinal axis extending along a longitudinal axis of the balloon;
the expandable portion further comprises a first common attachment component and a second common attachment component; and
each of the struts extends between the first common attachment component and the second common attachment component.

20. The intravascular device of claim 19 further comprising:
- an inner sleeve extending within the catheter tube and connected to said tip member.

* * * * *

UNITED STATES PATENT AND TRADEMARK OFFICE
CERTIFICATE OF CORRECTION

| | | |
|---|---|---|
| PATENT NO. | : 12,408,932 B2 | Page 1 of 1 |
| APPLICATION NO. | : 17/702336 | |
| DATED | : September 9, 2025 | |
| INVENTOR(S) | : John P. Pigott et al. | |

It is certified that error appears in the above-identified patent and that said Letters Patent is hereby corrected as shown below:

In the Claims

Column 13, Line 14, please insert --provided at-- after an incising element.

Signed and Sealed this
Fourth Day of November, 2025

John A. Squires
*Director of the United States Patent and Trademark Office*